US006294559B1

(12) United States Patent
Smith

(10) Patent No.: US 6,294,559 B1
(45) Date of Patent: Sep. 25, 2001

(54) ANTIPROLIFERATIVE AGENTS ASSOCIATED WITH PEROXISOME PROLIFERATOR ACTIVATED RECEPTORS GAMMA1 AND GAMMA2

(75) Inventor: Roy G. Smith, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/128,142

(22) Filed: Aug. 3, 1998

Related U.S. Application Data

(62) Division of application No. 08/844,007, filed on Apr. 18, 1997, now abandoned
(60) Provisional application No. 60/016,694, filed on May 2, 1996, now abandoned.

(51) Int. Cl.[7] .......................... A61K 31/425; A61K 31/41

(52) U.S. Cl. ........................... 514/369; 514/359; 514/365

(58) Field of Search ...................................... 514/369, 359, 514/365

(56) References Cited

U.S. PATENT DOCUMENTS 5,594,015 * 1/1997 Kuntz et al. .......................... 514/369

FOREIGN PATENT DOCUMENTS 0177353    4/1986  (EP) .

OTHER PUBLICATIONS

Zhu, et al., "Cloning of a New Member of the Peroxisome Proliferator–activated Receptor Gene . . . ", J. of Biol. Chem., vol. 268, No. 36, pp. 26817–26820, Dec. 25, 1993.
Greene, et al., "Isolation of the Human Peroxisome Proliferator Activated Receptor Gamma cDNA: Expression . . . ", Gene Expression, vol. 4, pp. 281–2999, 1993.
Tontonoz, et al., "Stimulation of Adipogenesis in Fibroblasts by PPARy2, a Lipid–Activated Transcription Factor", Cell, vol. 79, pp. 1147–1156, Dec. 30, 1994.
Forman, et al., "15–Deoxy— 12,14–Prostaglandin J2 is a Ligand for the Adipocyte Determination Factor PPARy", Cell, vol. 83, pp. 803–812, Dec. 1, 1995.
Kliewer, et al., "A Prostaglandin J2 Metabolite Binds Peroxisome Proliferator–Activated Receptor y and Promotes . . . ", Cell, vol. 83, pp. 813–819, Dec. 1, 1995.
Lehmann, et al., "An Antidiabetic Thiazolidinedione is a High Affinity Ligand for Peroxisome Proliferator . . . ", J. of Biol. Chem., vol. 270, No. 22, pp. 12953–12956, Jun. 2, 1995.
Elbrecht, et al., "Molecular Cloning, Expression and Characterization of Human Peroxisome Proliferator . . . ", Biochem. and Biophys. Res. Comm., vol. 224, pp. 431–437, 1996.
Santoro, et al., "PGJ2, A New Antiviral Prostaglandin: Inhibition of Sendai Virus Replication and Alteration . . . ", J. Gen. Virol., vol. 68, pp. 1153–1158, 1987.

Dreyer, et al., "Control of the Peroxisomal B–Oxidation Pathway by a Novel Family of Nuclear Hormone Receptors", Cell, vol. 68, pp. 879–887, Mar. 6, 1992.
Chen, et al., "Identification of Two mPPAR Related Receptors and Evidence for the Existence . . . ", Biochem. and Biophys. Res. Comm., vol. 196, No. 2, pp. 671–677, Oct. 29, 1993.
Kliewer, et al., "Differential expression and activation of a family of murine peroxisome proliferator . . . ", Proc. Natl. Acad. Sci. USA, vol. 91, pp. 7355–7359, Jul. 1994.
Tontonoz, et al., "mPPARy: tissue–specific regulator of an adipocyte enhancer", Genes & Development, vol. 8, pp. 1224–1234, 1994.
Zhu, et al., "Structural organization of mouse peroxisome proliferator–activated receptor y (mPPARy) gene . . .", Proc. Natl. Adac. Sci. USA, vol. 92, pp. 7921–7925, Aug. 1995.
Aperlo, et al., "cDNA cloning and characterization of the transcriptional activties of the hamster peroxisome . . . ", Gene, vol. 162, pp. 297–302, 1995.
Duvic et al 111CA:225334, 1988.*
Hughes–Fulford, et al., "Inhibition of DNA Synthesis and Cell Cycle by Prostaglandins Independent of Cyclic AMP", Advances in Prostaglandin, Thromboxanee and Leukotriene Research, vol. 15, pp. 401–404, 1985.
Lacal, et al., "Effects of Cyclopentenone Prostaglandins on Myeloid Cells during Early Infection with HTLV–1.II. Regulation of Synthesis of Inducible p72 Heat Shock Protein", Journal of Pharmacology and Experimental Therapeutics, vol. 271, No. 2, pp. 10096–1102, 1994.
Mueller, et al., "Terminal Differentiation of Human Breast Cancer through PPARγ", Molecular Cell, vol. 1, pp. 465–470, Feb. 1998.
Narumiya, et al., "Site and Mechanism of Growth Inhibition by Prostaglandins. I. Active Transport and Intracellular Accumulation of Cyclopentenone Prostaglandins . . . ", Journal of Pharmacol. and Exp. Therap., vol. 239, No. 2, pp. 500–505, 1986.
Narumiya, et al., "Site and Mechanism of Growth Inhibition by Prostaglandins. II. Temperature–Dependent Transfer of a Cyclopentenone Prostaglandin to Nuclei", Journal of Pharmacol. and Exp Therap., vol. 239, No. 2, pp. 506–511, 1986.
Rozera, et al., "Inhibition of HIV–1 Replication by Cyclopentenone Prostaglandins in Acutely Infected Human Cells", J. Clin. Invest., vol. 97, No. 8, Apr. 1996, pp. 1795–1803.
Santoro, et al., "Involvement of Protein Synthesis in the Antiproliferative and the Antiviral Action of Prostaglandins", Prostaglandins in Cancer Research, pp. 97–114.

(List continued on next page.)

Primary Examiner—Russell Travers
(74) Attorney, Agent, or Firm—Joseph A. Coppola; Jack L. Tribble

(57) ABSTRACT

This invention is directed to compounds and ligands that bind to peroxisome proliferator activated receptors (PPAR) γ1 and γ2 and which function as antiproliferative, antiviral and antitumour agents. The invention is also directed to the use of PPAR γ1 and γ2 to identify such compounds and methods of using the compounds for medical uses.

3 Claims, 7 Drawing Sheets

OTHER PUBLICATIONS

Santoro, et al., "PGJ2, A New Antiviral Prostaglandin: Inhibition of Sendai Virus Replication and Alteration of Virus Protein Synthesis", J. Gen. Virol., vol. 68, pp. 1153–1158, 1987.

Sasaki, et al., "Prostaglandins in the treatment of cancer", Anti–Cancer Drugs, vol. 5, pp. 131–138, 1994.

Xing, et al., "Rat PPARδ Contains A CGG Triplet Repeat and Is Prominently Expressed in the ThalamicNuclei", Biochem. and Biophys. Res. Comm., vol. 217, No. 3, 1995, pp. 1015–1025.

* cited by examiner

```
   1  ATGACCATGG TTGACACAGA GATGCCATTC TGGCCCACCA ACTTTGGGAT CAGCTCCGTG
  61  GATCTCTCCG TAATGGAAGA CCACTCCCAC TCCTTTGATA TCAAGCCCTT CACTACTGTT
 121  GACTTCTCCA GCATTCTAC TCCACATTAC GAAGACATTC CATTCACACAG AACAGATCCA
 181  GTGGTTGCAG ATTACAAGTA TGACCTGAAA CTTCAAGAGT AAGACTCAGC ACCAAAGTGC AATCAAAGTG
 241  GAGCCTGCAT CTCCACCTTA TTATTCTGAG AAGACTCAGC TCTACAATAA GCCTCATGAA
 301  GAGCCTTCCA ACTCCCTCAT GGCAATTGAA TGTCGTGTCT GTGGAGATAA AGCTTCTGGA
 361  TTTCACTATG GAGTTCATGC TTGTGAAGGA TGCAAGGGTT TCTTCCGAG AACAATCAGA
 421  TTGAAGCTTA TCTATGACAG ATGTGATCTT AACTGTCGGA TCCACAAAAA AAGTAGAAAT
 481  AAATGTCAGT ACTGTCGGTT TCAGAAATGC CTTGCAGTGG GGATGTCTCA TAATGCCATC
 541  AGTTTGGGC GGATGCCACA GCCCGAGAAG GAGAAGCTGT TGGCGGAGAT CTCCAGTGAT
 601  ATCGACCAGC TGAATCCAGA GTCCGCTGAC CTCCGGGCCC TGGCAAAACA TTTGTATGAC
 661  TCATACATAA AGTCCTTCCC GCTGACCAAA GCAAAGGCGA GGGCGATCTT GACAGGAAAG
 721  ACAACAGACA AATCACCATT CGTTATCTAT CACCCCCCCTG CCTTAATGAT GGGAGAAGAT
 781  AAAATCAAGT GCTGCCAGTT TCGCTCCCGTG CAGGAGCAGA GCAAAGAGGT GGCCATCCGC
 841  ATCTTTCAGG GCTGCCAGTT AAATCTTGAC TGCTCCGTG AGGAGATCAC AGAGTATGCC
 901  AAAAGCATTC CTGGTTTTGT CACACATTA TTGAACGACC AAGTAACTCT CCTCAAATAT
 961  GGAGTCCACC AGATCATTTA CACAAGGCTT GCCCTCCTGA TGAATAAAGA TGGGGTTCTC
1021  ATATCCGAGG GCCAAGGCTT CATGACAAGG GAGTTTCTAA AGAGCCTGCG AAAGCCTTTT
1081  GGTGACTTTA TGGAGCCCAA GTTTGAGTTT GCTGTGAAGT TCAATGCACT GGAATTAGAT
1141  GACAGCGACT TGGCAATATT TATTGCTGTC ATTATTCTCA GTGGAGACCG CCCAGGTTTG
1201  CTGAATGTGA AGCCCATTGA AGACATTCAA GACAACCTGC TACAAGCCCT GGAGCTCCAG
1261  CTGAAGCTGA ACCACCCTGA GTCCTCACAG CTGTTGCCA AGCTGCTCCA GAAAATGACA
1321  GACCTCAGAC AGATTGTCAC GGAACACGTG CAGCTACTGC AGGTGATCAA GAAGACGGAG
1381  ACAGACATGA GTCTTCACCC GCTCCTGCAG GAGATCTACA AGGACTGTA CTAG (SEQ ID NO:1)
```

FIG.1

```
  1  MTMVDTEMPF  WPTNFGISSV  DLSVMEDHSH  SFDIKPFTTV  DFSSISTPHY  EDIPFTRTDP
 61  VVADYKYDLK  LQEYQSAIKV  EPASPPYYSE  KTQLYNKPHE  EPSNSLMAIE  CRVCGDKASG
121  FHYGVHACEG  CKGFFRRTIR  LKLIYDRCDL  NCRIHKKSRN  KCQYCRFQKC  LAVGMSHNAI
181  RFGRMPQAEK  EKLLAEISSD  IDQLNPESAD  LRALAKHLYD  SYIKSFPLTK  AKARAILTGK
241  TTDKSPFVIY  DMNSLMMGED  KIKFKHITPL  QEQSKEVAIR  IFQGCQFRSV  EAVQEITEYA
301  KSIPGFVNLD  LNDQVTLLKY  GVHEIIYTML  ASLMNKDGVL  ISEGQGFMTR  EFLKSLRKPF
361  GDFMEPKFEF  AVKFNALELD  DSDLAIFIAV  IILSGDRPGL  LNVKPIEDIQ  DNLLQALELQ
421  LKLNHPESSQ  LFAKLLQKMT  DLRQIVTEHV  QLLQVIKKTE  TDMSLHPLLQ  EIYKDLY (SEQ ID NO:2)
```

FIG.2

```
   1  ATGGGTGAAA CTCTGGGAGA TTCTCCTATT GACCCAGAAA GCGATTCCTT CACTGATACA
  61  CTGTCTGCAA ACATATCACA AGAAATGACC ATGGTTGACA CAGAGATGCC ATTCTGGCCC
 121  ACCAACTTTG GGATCAGCTC CGTGGATCTC TCCGTAATGG AAGACCACTC CCACTCCTTT
 181  GATATCAAGC CCTTCACTAC TGTTGACTTC TCCAGCATTT CTACTCCACA TTACGAAGAC
 241  ATTCCATTCA CAAGAACAGA TCCAGTGGTT GCAGATTACA AGTATGACCT GAAACTTCAA
 301  GAGTACCAAA GTGCAATCAA AGTGGAGCCT GCATCTCCAC CTTATTATTC TGAGAAGACT
 361  CAGCTCTACA ATAAGCCTCA TGAAGAGCCT TCCAACTCCC TCATGGCAAT TGAATGTCGT
 421  GTCTGTGGAG ATAAAGCTTC TGGATTTCAC TATGGAGTTC ATGCTTGTGA AGGATGCAAG
 481  GGTTTCTTCC GGAGAACAAT CAGATTGAAG CTTATCTATG ACAGATGTGA TCTTAACTGT
 541  CGGATCCACA AAAAAAGTAG AAATAAATGT CAGTACTGTC GGTTTCAGAA ATGCCTTGCA
 601  GTGGGATGT CTCATAATGC CATCAGGTTT GGGCGGATGC CACAGGCCCA GAAGGAGAAG
 661  CTGTTGGCCG AGATCTCCAG TGATATCGAC TGATATCCAG CAGAGTCCGC TGACCTCCGG
 721  GCCCTGGCAA AACATTTGTA TGACTCATAC ATAAAGTCCT TCCCGCTGAC CAAAGCAAAG
 781  GCGAGGGCGA TCTTGACAGG AAAGACAACA GACAAATCAC CATTCGTTAT CTATGACATG
 841  AATTCCTTAA TGATGGGAGA AGATAAAATC AAGTTCAAAC ACATCACCCC CCTGCAGGAG
 901  CAGAGCAAAG AGGTGGCCAT CCGCATCTTT CAGGGCTGCC AGTTTCGCTC CGTGGAGGCT
 961  GTGCAGGAGA TCACAGAGTA TGCCAAAAGC ATTCCTGGTT TTGTAAATCT TGACTTGAAC
1021  GACCAAGTAA CTCTCCTCAA ATATGGAGTC CACGAGATCA TTTACACAAT GCTGGCCTCC
1081  TTGATGAATA AAGATGGGGT TCTCATATCC GAGGGCCAAG GCTTCATGAC AAGGGAGTTT
1141  CTAAAGAGCC TGCGAAAGCC TTTTGGTGAC TTTATGGAGC CCAAGTTTGA GTTGCTGTG
1201  AAGTTCAATG CACTGGAATT AGATGACAGC GACTTGGCAA TATTTATTGC TGTCATTATT
1261  CTCAGTGGAG ACCGCCCAGG CCTGGAGCT GTGAAGCCCA TTGAAGACAT TCAAGACAAC
1321  CTGCTACAAG CCCTGGAGCT CCAGCTGAAG CTGAACCACC CTGAGTCCTC ACAGCTGTTT
1381  GCCAAGCTGC TCCAGAAAAT GACAGACCTC AGACAGATTG TCACGGAACA CGTGCAGCTA
1441  CTGCAGGTGA TCAAGAAGAC GGAGACAGAC ATGAGTCTTC ACCCGCTCCT GCAGGAGATC
1501  TACAAGGACT TGTACTAG          (SEQ ID NO:3)
```

FIG.3

```
  1  MGETLGDSPI  DPESDSFTDT  LSANISQEMT  MVDTEMPFWP  TNFGISSVDL  SVMEDHSHSF
 61  DIKPFTTVDF  SSISTPHYED  IPFTRTDPVV  ADYKYDLKLQ  EYQSAIKVEP  ASPPYYSEKT
121  QLYNKPHEEP  SNSLMAIECR  VCGDKASGFH  YGVHACEGCK  GFFRRTIRLK  LIYDRCDLNC
181  RIHKKSRNKC  QYCRFQKCLA  VGMSHNAIRF  GRMPQAEKEK  LLAEISSDID  QLNPESADLR
241  ALAKHLYDSY  IKSFPLTKAK  ARAILTGKTT  DKSPFVIYDM  NSLMMGEDKI  KFKHITPLQE
301  QSKEVAIRIF  QGCQFRSVEA  VQEITEYAKS  IPGFVNLDLN  DQVTLLKYGV  HEIIYTMLAS
361  LMNKDGVLIS  EGQGFMTREF  LKSLRKPFGD  FMEPKFEFAV  KFNALELDDS  DLAIFIAVII
421  LSGDRPGLLN  VKPIEDIQDN  LLQALELQLK  LNHPESSQLF  AKLLQKMTDL  RQIVTEHVQL
481  LQVIKKTETD  MSLHPLLQEI  YKDLY  (SEQ ID NO:4)
```

FIG. 4

| THIAZOLIDINEDIONE | RECEPTOR ISOFORM | BINDING IC$_{50}$ (nm) | TRANSACTIVATION | |
|---|---|---|---|---|
| | | | EC$_{50}$ (nm) | FOLD ACTIVATION |
| AD-5075 | hPPARγ1 | 31 | 1 | 4.5 |
| | hPPARγ2 | 33 | 1 | 3.4 |
| BRL 49653 | hPPARγ1 | 307 | 86 | 4.1 |
| | hPPARγ2 | 360 | 95 | 4.3 |
| CS-045 | hPPARγ1 | 3000 | 740 | 4.9 |
| | hPPARγ2 | 4000 | 1600 | 4.4 |

FIG. 7

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 1434 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
ATGACCATGG TTGACACAGA GATGCCATTC TGGCCCACCA ACTTTGGGAT CAGCTCCGTG      60

GATCTCTCCG TAATGGAAGA CCACTCCCAC TCCTTTGATA TCAAGCCCTT CACTACTGTT     120

GACTTCTCCA GCATTTCTAC TCCACATTAC GAAGACATTC CATTCACAAG AACAGATCCA     180

GTGGTTGCAG ATTACAAGTA TGACCTGAAA CTTCAAGAGT ACCAAAGTGC AATCAAAGTG     240

GAGCCTGCAT CTCCACCTTA TTATTCTGAG AAGACTCAGC TCTACAATAA GCCTCATGAA     300

GAGCCTTCCA ACTCCCTCAT GGCAATTGAA TGTCGTGTCT GTGGAGATAA AGCTTCTGGA     360

TTTCACTATG GAGTTCATGC TTGTGAAGGA TGCAAGGGTT TCTTCCGGAG AACAATCAGA     420

TTGAAGCTTA TCTATGACAG ATGTGATCTT AACTGTCGGA TCCACAAAAA AAGTAGAAAT     480

AAATGTCAGT ACTGTCGGTT TCAGAAATGC CTTGCAGTGG GGATGTCTCA TAATGCCATC     540

AGGTTTGGGC GGATGCCACA GGCCGAGAAG GAGAAGCTGT TGGCGGAGAT CTCCAGTGAT     600

ATCGACCAGC TGAATCCAGA GTCCGCTGAC CTCCGGGCCC TGGCAAAACA TTTGTATGAC     660

TCATACATAA AGTCCTTCCC GCTGACCAAA GCAAAGGCGA GGGCGATCTT GACAGGAAAG     720
```

-continued

```
ACAACAGACA AATCACCATT CGTTATCTAT GACATGAATT CCTTAATGAT GGGAGAAGAT    780

AAAATCAAGT TCAAACACAT CACCCCCCTG CAGGAGCAGA GCAAAGAGGT GGCCATCCGC    840

ATCTTTCAGG GCTGCCAGTT TCGCTCCGTG GAGGCTGTGC AGGAGATCAC AGAGTATGCC    900

AAAAGCATTC CTGGTTTTGT AAATCTTGAC TTGAACGACC AAGTAACTCT CCTCAAATAT    960

GGAGTCCACG AGATCATTTA CACAATGCTG GCCTCCTTGA TGAATAAAGA TGGGGTTCTC   1020

ATATCCGAGG GCCAAGGCTT CATGACAAGG GAGTTTCTAA AGAGCCTGCG AAAGCCTTTT   1080

GGTGACTTTA TGGAGCCCAA GTTTGAGTTT GCTGTGAAGT TCAATGCACT GGAATTAGAT   1140

GACAGCGACT TGGCAATATT TATTGCTGTC ATTATTCTCA GTGGAGACCG CCCAGGTTTG   1200

CTGAATGTGA AGCCCATTGA AGACATTCAA GACAACCTGC TACAAGCCCT GGAGCTCCAG   1260

CTGAAGCTGA ACCACCCTGA GTCCTCACAG CTGTTTGCCA AGCTGCTCCA GAAAATGACA   1320

GACCTCAGAC AGATTGTCAC GGAACACGTG CAGCTACTGC AGGTGATCAA GAAGACGGAG   1380

ACAGACATGA GTCTTCACCC GCTCCTGCAG GAGATCTACA AGGACTTGTA CTAG         1434
```

(2) INFORMATION FOR SEQ ID NO: 2:

(i) SEQUENCE CHARACTERISTICS:
        (A) LENGTH: 477 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Met Thr Met Val Asp Thr Glu Met Pro Phe Trp Pro Thr Asn Phe Gly
1               5                   10                  15

Ile Ser Ser Val Asp Leu Ser Val Met Glu Asp His Ser His Ser Phe
                20                  25                  30

Asp Ile Lys Pro Phe Thr Thr Val Asp Phe Ser Ser Ile Ser Thr Pro
            35                  40                  45

His Tyr Glu Asp Ile Pro Phe Thr Arg Thr Asp Pro Val Val Ala Asp
        50                  55                  60

Tyr Lys Tyr Asp Leu Lys Leu Gln Glu Tyr Gln Ser Ala Ile Lys Val
65                  70                  75                  80

Glu Pro Ala Ser Pro Pro Tyr Tyr Ser Glu Lys Thr Gln Leu Tyr Asn
                85                  90                  95

Lys Pro His Glu Glu Pro Ser Asn Ser Leu Met Ala Ile Glu Cys Arg
            100                 105                 110

Val Cys Gly Asp Lys Ala Ser Gly Phe His Tyr Gly Val His Ala Cys
        115                 120                 125

Glu Gly Cys Lys Gly Phe Phe Arg Arg Thr Ile Arg Leu Lys Leu Ile
    130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Met Pro Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Ala Leu Ala Lys His Leu Tyr Asp Ser Tyr Ile Lys
    210                 215                 220
```

```
Ser Phe Pro Leu Thr Lys Ala Lys Ala Arg Ala Ile Leu Thr Gly Lys
225                 230                 235                 240

Thr Thr Asp Lys Ser Pro Phe Val Ile Tyr Asp Met Asn Ser Leu Met
                245                 250                 255

Met Gly Glu Asp Lys Ile Lys Phe Lys His Ile Thr Pro Leu Gln Glu
            260                 265                 270

Gln Ser Lys Glu Val Ala Ile Arg Ile Phe Gln Gly Cys Gln Phe Arg
        275                 280                 285

Ser Val Glu Ala Val Gln Glu Ile Thr Glu Tyr Ala Lys Ser Ile Pro
290                 295                 300

Gly Phe Val Asn Leu Asp Leu Asn Asp Gln Val Thr Leu Leu Lys Tyr
305                 310                 315                 320

Gly Val His Glu Ile Ile Tyr Thr Met Leu Ala Ser Leu Met Asn Lys
                325                 330                 335

Asp Gly Val Leu Ile Ser Glu Gly Gln Gly Phe Met Thr Arg Glu Phe
            340                 345                 350

Leu Lys Ser Leu Arg Lys Pro Phe Gly Asp Phe Met Glu Pro Lys Phe
        355                 360                 365

Glu Phe Ala Val Lys Phe Asn Ala Leu Glu Leu Asp Asp Ser Asp Leu
370                 375                 380

Ala Ile Phe Ile Ala Val Ile Ile Leu Ser Gly Asp Arg Pro Gly Leu
385                 390                 395                 400

Leu Asn Val Lys Pro Ile Glu Asp Ile Gln Asp Asn Leu Leu Gln Ala
                405                 410                 415

Leu Glu Leu Gln Leu Lys Leu Asn His Pro Glu Ser Ser Gln Leu Phe
            420                 425                 430

Ala Lys Leu Leu Gln Lys Met Thr Asp Leu Arg Gln Ile Val Thr Glu
        435                 440                 445

His Val Gln Leu Leu Gln Val Ile Lys Lys Thr Glu Thr Asp Met Ser
450                 455                 460

Leu His Pro Leu Leu Gln Glu Ile Tyr Lys Asp Leu Tyr
465                 470                 475
```

(2) INFORMATION FOR SEQ ID NO: 3:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
ATGGGTGAAA CTCTGGGAGA TTCTCCTATT GACCCAGAAA GCGATTCCTT CACTGATACA      60

CTGTCTGCAA ACATATCACA AGAAATGACC ATGGTTGACA CAGAGATGCC ATTCTGGCCC     120

ACCAACTTTG GGATCAGCTC CGTGGATCTC TCCGTAATGG AAGACCACTC CCACTCCTTT     180

GATATCAAGC CCTTCACTAC TGTTGACTTC TCCAGCATTT CTACTCCACA TTACGAAGAC     240

ATTCCATTCA CAAGAACAGA TCCAGTGGTT GCAGATTACA AGTATGACCT GAAACTTCAA     300

GAGTACCAAA GTGCAATCAA AGTGGAGCCT GCATCTCCAC TTATTATTC TGAGAAGACT      360

CAGCTCTACA ATAAGCCTCA TGAAGAGCCT TCCAACTCCC TCATGGCAAT TGAATGTCGT     420

GTCTGTGGAG ATAAAGCTTC TGGATTTCAC TATGGAGTTC ATGCTTGTGA AGGATGCAAG     480

GGTTTCTTCC GGAGAACAAT CAGATTGAAG CTTATCTATG ACAGATGTGA TCTTAACTGT     540
```

-continued

```
CGGATCCACA AAAAAAGTAG AAATAAATGT CAGTACTGTC GGTTTCAGAA ATGCCTTGCA    600
GTGGGGATGT CTCATAATGC CATCAGGTTT GGGCGGATGC CACAGGCCGA GAAGGAGAAG    660
CTGTTGGCGG AGATCTCCAG TGATATCGAC CAGCTGAATC CAGAGTCCGC TGACCTCCGG    720
GCCCTGGCAA ACATTTGTA TGACTCATAC ATAAAGTCCT TCCCGCTGAC CAAAGCAAAG     780
GCGAGGGCGA TCTTGACAGG AAAGACAACA GACAAATCAC CATTCGTTAT CTATGACATG    840
AATTCCTTAA TGATGGGAGA AGATAAAATC AAGTTCAAAC ACATCACCCC CCTGCAGGAG    900
CAGAGCAAAG AGGTGGCCAT CCGCATCTTT CAGGGCTGCC AGTTTCGCTC CGTGGAGGCT    960
GTGCAGGAGA TCACAGAGTA TGCCAAAAGC ATTCCTGGTT TTGTAAATCT TGACTTGAAC   1020
GACCAAGTAA CTCTCCTCAA ATATGGAGTC CACGAGATCA TTTACACAAT GCTGGCCTCC   1080
TTGATGAATA AAGATGGGGT TCTCATATCC GAGGGCCAAG GCTTCATGAC AAGGGAGTTT   1140
CTAAAGAGCC TGCGAAAGCC TTTTGGTGAC TTTATGGAGC CCAAGTTTGA GTTTGCTGTG   1200
AAGTTCAATG CACTGGAATT AGATGACAGC GACTTGGCAA TATTTATTGC TGTCATTATT   1260
CTCAGTGGAG ACCGCCCAGG TTTGCTGAAT GTGAAGCCCA TTGAAGACAT TCAAGACAAC   1320
CTGCTACAAG CCCTGGAGCT CCAGCTGAAG CTGAACCACC CTGAGTCCTC ACAGCTGTTT   1380
GCCAAGCTGC TCCAGAAAAT GACAGACCTC AGACAGATTG TCACGGAACA CGTGCAGCTA   1440
CTGCAGGTGA TCAAGAAGAC GGAGACAGAC ATGAGTCTTC ACCCGCTCCT GCAGGAGATC   1500
TACAAGGACT TGTACTAG                                                 1518
```

(2) INFORMATION FOR SEQ ID NO: 4:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
    50                  55                  60

Phe Thr Thr Val Asp Phe Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175
```

```
Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
        210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
        290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
            355                 360                 365

Ile Ser Glu Gly Gln Gly Phe Met Thr Arg Glu Phe Leu Lys Ser Leu
        370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
        435                 440                 445

Leu Lys Leu Asn His Pro Glu Ser Ser Gln Leu Phe Ala Lys Leu Leu
    450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
            485                 490                 495

Leu Gln Glu Ile Tyr Lys Asp Leu Tyr
            500                 505
```

ANTIPROLIFERATIVE AGENTS ASSOCIATED WITH PEROXISOME PROLIFERATOR ACTIVATED RECEPTORS GAMMA1 AND GAMMA2

This application is a divisional of U.S. patent application Ser. No. 08/844,007, filed Apr. 18, 1997, now abandoned, which claims the benefit of U.S. Provisional Application No. 60/016,694, filed May 2, 1996.

CROSS-REFERENCE TO RELATED APPLICATIONS

Not applicable.

STATEMENT REGARDING FEDERALLY-SPONSORED R&D

Not applicable.

REFERENCE TO MICROFICHE APPENDIX

Not applicable.

FIELD OF THE INVENTION

This invention is directed to ligands that bind to human peroxisome proliferator activated receptors (PPAR) γ1 and γ2. The ligands are useful as antiviral, antiproliferative and antitumor agents

BACKGROUND OF THE INVENTION

This disclosure is directed to ligands that bind to peroxisome proliferator activated receptors (PPAR) γ1 or γ2 and which function as antiproliferative agents. The invention is also directed to the use of PPAR γ1 or γ2 to identify compounds that are antiproliferative agents. This disclosure is further directed to new medical uses of these compounds.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of hyperlipidemic drugs, herbicides and phthalate plasticizers. Peroxisome proliferation is also triggered by dietary or physiological factors such as a high-fat diet and cold acclimatization.

Identification of a member of the nuclear hormone receptor superfamily activated by these chemicals has facilitated analysis of the mechanism by which peroxisome proliferators exert their pleiotropic effects. This receptor, known as peroxisome proliferator activated receptor alpha (PPAR), is activated by a number of medium and long-chain fatty acids. The receptor stimulates expression of genes encoding rat acyl-CoA oxidase and hydratase-dehydrogenase.

The PPAR γ receptor subtypes are involved in activating the program of adipocyte differentiation and are not involved in stimulating peroxisome proliferation in the liver. There are two isoforms of PPAR gamma: PPAR γ1 (PPARγ1) and PPAR γ2 (PPARγ2), which differ only in that PPARγ2 contains an additional 28 amino acids present at the amino terminus. In mice, PPARγ2 is expressed specifically in fat cells. Tontonoz et al., Cell 79: 1147–1156 [1994] provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements for example in the 5' flanking regions of responsive genes. An example of a PPARγ2 responsive gene is the tissue-specific adipocyte P2 gene.

Three classes of ligands have been identified for the PPARγ receptors. Prostaglandin $J_2$ could represent an endogenous class of ligands (Forman et al. Cell 83: 803–812 [1995], Kliewer et al. Cell 83: 813–819 [1995]), while the thiazolidinediones could represent another class (Lehman et al. J. Biol. Chem 270: 12953–12956 [1995]). A third class of ligands is represented by a new series of MRL compounds. The thiazolidinediones and MRL compounds are antidiabetic compounds effective in reducing glucose, lipid and insulin levels in rodent models. Thus, novel PPARγ ligands and regulators could be used in the treatment of diabetes and effect fat cell differentiation. In addition, cyclopentanone prostaglandins having structural similarity to Prostaglandin J2 have been described to have antiproliferative and antiviral properties (C. Rozera et al., J. Clin. Invest. 97:1795–1803; M. Santoro et al., J. Gen. Virol. 68:1153–1158; Sasaki and Fukushima, Anti-Cancer Drugs 5:131–138). Other compounds of this class of prostaglandins but the bind to PPAR γ receptor subtypes will also have antiproliferative and antivral properties.

SUMMARY OF THE INVENTION

This invention is directed to compounds and ligands that bind to peroxisome proliferator activated receptors (PPAR) γ1 and γ2 and which function as antiproliferative, antiviral and antitumor agents. The invention is also directed to the use of PPAR γ1 and γ2 to identify compounds that are antiproliferative, antiviral or antitumor agents. (The invention is further directed to the medical use of the antiproliferative, antiviral and antitumor agents.)

BRIEF DESCRIPTION OF THE DRAWINGS

FIG. 1 shows the nucleotide sequence of PPAR γ1 (SEQ ID NO: 1).

FIG. 2 shows the amino acid sequence of PPAR γ1 (SEQ ID NO:2).

FIG. 3 shows the nucleotide sequence of PPAR γ2 (SEQ ID NO:3).

FIG. 4 shows the amino acid sequence of PPAR γ2 (SEQ ID NO:4).

FIG. 7 is Table 1. Table 1 shows that thiazolidinediones bind to and activate hPPAR gamma 1 and hPPAR gamma 2.

DETAILED DESCRIPTION OF THE INVENTION

This invention is directed to compounds and ligands that bind to peroxisome proliferator activated receptors (PPAR)

γ1 and γ2 and which function as antiproliferative, antiviral or antitumor agents. The invention is also directed to the use of PPAR γ1 and γ2 to identify such compounds. (The invention is further directed to the medical use of the antiproliferative, antiviral and antitumor agents.)

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of hypolipidermic drugs, herbicides and phthalate plasticizers. Peroxisome proliferation is also triggered by dietary or physiological factors such as a high-fat diet and cold acclimatization.

Identification of a member of the nuclear hormone receptor superfamily activated by these chemicals has facilitated analysis of the mechanism by which peroxisome proliferators exert their pleiotropic effects. This receptor, known as peroxisome proliferator activated receptor alpha (PPARα), is activated by a number of medium and long-chain fatty acids. The receptor stimulates expression of genes encoding rat acyl-CoA oxidase and hydratase-dehydrogenase.

Figure 5:
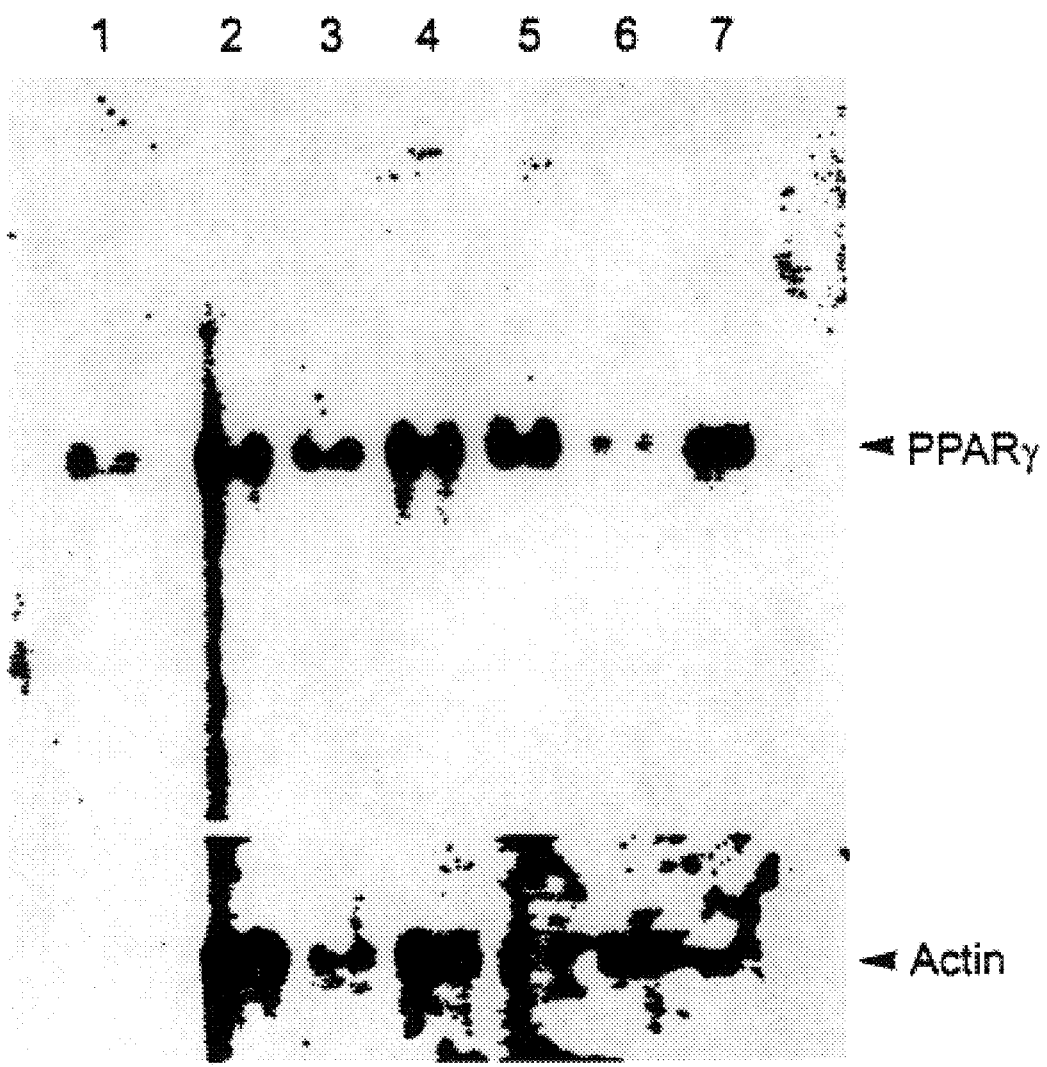
FIG. 5. Expression of PPARγ mRNA in human tissues. The Northern blot was generated using the entire translated portion of PPARγ2 cDNA as a probe (upper panel) lane 1: 15 μg of total cellular RNA from human adipocytes; lanes 2–7: 5 μg of poly (A)$^+$ RNA form human bone marrow, skeletal muscle, spleen, testis, brain and liver, respectively. The filter was stripped and rehybridized with a probe for human β-actin (lower panel).
Figure 6:
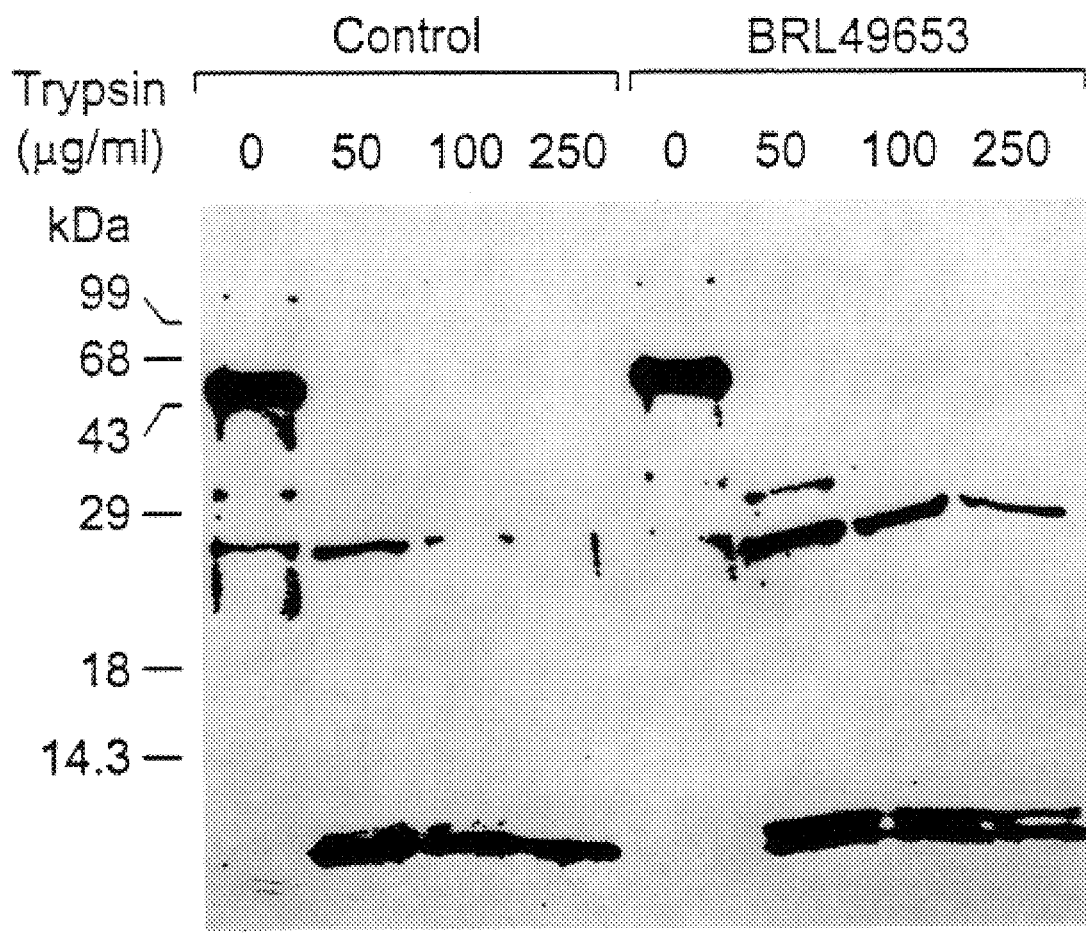
FIG. 6. A thiazolidinedione produces a partially protease resistant conformation of hPPARγ1. [$^{35}$S]hPPARγ1 was synthesized in vitro in a coupled transcription/translation system. It was subsequently preincubated with 0.1% DMSO (Control) or 10 μM of a thiazolidinedione and then incubated with dH$_2$O or increasing concentrations of trypsin. Digestion products were analyzed by SDS-PAGE followed by autoradiography. An asterisk indicates the 27 kDa protease resistant fragment of hPPARγ1.

PPARγ is a related PPAR subtype which is not involved in mediating peroxisome proliferation, but which may have a role in regulation of adipocyte differentiation and gene expression.. PPARγ isoforms (γ1 and/or γ2) have been cloned from a number of different eukaryotic species. Xenopus PPAR γ was reported by Dreyer et al. Cell 68:879–887 [1992]. Murine PPAR γ1 was reported by Zhu et al. J. Biol. Chem. 268:26817–26820 [1993], Chen et al. Biochem. Biophys. Res. Comm. 196:671–677 [1993], and Kliewer et al. Proc. Natl. Acad. Sci. 91:7355–7359 [1994]. Murine PPAR γ2 was reported by Tontonoz et al. Genes and Devel. 8:1224–1234 [1994] and Zhu et al. Proc. Natl. Acad. Sci. 92:7921–7925 [1995]. Hamster PPAR γ1 was reported by Aperlo et al. Gene 162:297–302 [1995]. A human PPAR γ1 cDNA was also reported by Greene et al. Gene Expression 4:281–299 [1995]. Additional human PPAR γ1 and γ2 cDNAs were cloned and sequenced; sequences (nucleotide and amino acid) are depicted in FIGS. 1–4. The predicted protein structure of mammalian PPAR γ1 vs. γ2 isoforms involves an additional 28–30 amino acids which are present at the amino-(N–) terminus of PPAR γ2 and are not present in PPAR γ2 (Zhu et al. Proc. Natl. Acad. Sci. 92:7921–7925 [1995]). It is clear that various known compounds, such as thiazolidinediones, bind with high affinity and mediate activation of both PPAR γ1 and PPAR γ2 isoforms (Lehmann et al. J. Biol. Chem. 270:12953–12956 [1995]). Furthermore, the expression pattern of PPARg in mammalian tissues is not restricted to fat (Vidal-Puig et al, J. Clin. Invest., 1996, in press; Zhu et al. J. Biol. Chem. 263:26817–26820, 1993, FIG. 5). Therefore, what is claimed is that ligands or agents which bind to, and/or modulate the functions of, any or all isoforms of PPAR γ derived from any or all species, can have utility as anti-viral, anti-proliferative, or anti-cancer agents:

Examples of compounds that modulate the functions of PPAR γ receptors include, but are not limited to cyclopentenone prostaglandins and thiazolidinediones. The thiazolidinediones (glitazones) are a class of compounds associated with ameliorating symptoms of noninsulin dependent diabetes mellitus.

In addition to known (and unknown) compounds that modulate the function(s) of PPARγ, pharmaceutically useful compositions comprising the PPARγ DNA sequences or proteins encoded by the DNA may be used in a way that can achieve antiproliferative, antitumor and antiviral effects. These agents may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein.

Therapeutic compositions of the invention are administered to an individual in amounts sufficient to modulate PPARγ1 or PPARγ2 and to treat disorders related to but not limited to, excessive cell proliferation, cancer and viral invection. The effective amount may vary according to a variety of factors such as the individual's condition, weight, sex and age. Other factors include the mode of administration. Generally, the compositions will be administered in dosages ranging from about 1 μg to about 100 mg.

The pharmaceutical compositions may be provided to the individual by a variety of routes such as subcutaneous, topical, oral, mucosal, intravenous and intramuscular.

The compositions may be administered by a variety of routes, such as orally, parenterally, subcutaneously, mucosally, intravenously or intramuscularly. The dosage administered may vary with the condition, sex, weight, and age of the individual; the route of administration; and the type of composition. The composition may be used in dosage forms such as capsules, suspensions, elixirs, or liquid solutions. The composition may be formulated with an acceptable carrier. The composition may be administered in single or multiple doses.

The present invention is also directed to methods for screening for compounds which modulate the expression of DNA or RNA encoding PPARγ as well as the function(s) of PPARγ protein(s) in vivo, so as to achieve antiproliferative, antitumor or antiviral effects. Compounds which modulate these activities may be DNA, RNA, peptides, proteins, or non-proteinaceous organic molecules. Compounds may modulate by increasing or attenuating the expression of DNA or RNA encoding PPARγ, or the function of PPARg protein. Compounds that modulate the expression of DNA or RNA encoding PPARg or the function of PPARγ protein may be detected by a variety of assays. The assay may be a simple "yes/no" assay to determine whether there is a change in expression or function. The assay may be made quantitative by comparing the expression or function of a test sample with the levels of expression or function in a standard sample. The assay may be a competitive binding assay.

Nucleotide sequences that are complementary to the PPARγ encoding DNA sequences may be synthesized for antisense therapy. These antisense molecules may be DNA, stable derivatives of DNA such as phosphorothioates or methylphosphonates, RNA, stable derivatives of RNA such as 2'-O-alkylRNA, or other PPAR antisense oligonucleotide mimetics. PPAR antisense molecules may be introduced into cells by microinjection, liposome encapsulation or by expression from vectors harboring the antisense sequence. PPAR antisense therapy may be particularly useful for the treatment of diseases where it is beneficial to reduce PPAR activity.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain stimulation or inhibition of the PPAR or its activity while minimizing any potential toxicity. In addition, co-administration or sequential administration of other agents may be desirable.

Advantageously, compounds of the present invention may be administered in a single daily dose, or the total daily dosage may be administered in several divided doses. Furthermore, compounds for the present invention may be administered via a variety of routes including but not limited to intranasally, transdermally, by suppository, orally, and the like For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream of gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Compounds that affect PPAR activity may be detected by a variety of methods. A method of identifying compounds that affect PPAR comprises:

(a) mixing a test compound with a solution containing PPAR to form a mixture;

(b) measuring PPAR activity in the mixture; and (c) comparing the PPAR activity in the mixture to a standard.

Another method of identifying compounds that affect PPAR comprises:

(a) incubating a test compound with cells expressing PPAR;

(b) measuring PPAR activity in the cells or cell lysates; and (c) comparing the PPAR activity to a standard.

Compounds that affect PPAR activity may be formulated into pharmaceutical compositions. Such pharmaceutical compositions may be useful for treating conditions that are mediated by altered PPAR activity.

EXAMPLE 2

Compounds will be identified that bind with high affinity to PPARγ1 or PPARγ2 and transactivate a reporter gene containing a PPARγ DNA response element gene according to those skilled in the art. For example the adipocyte specific fatty acid binding protein (ap2) gene DNA response element could be used when coupled to an appropriated reporter gene such as luciferase or chloramphenicol acetyl transferase. The reporter gene would then be activated by addition of a test compound following its transfection into cells expressing PPARγ1 or PPARγ2. This test compound (ligand) so identified would have potential utility as an antiviral, antiproliferative or antitumor agent.

EXAMPLE 3

Expression of PPARγ1 and γ2 in COS-1 cells

Full-length cDNAs for PPARγ1 and PPARγ2 were subcloned into the pSG5 mammalian expression vector (Stratagene) to generate pSG/hPPARγ1, and pSG/hPPARγ2, respectively. COS-1 cells were seeded at $5 \times 10^3$ cells/well in 96 well cell culture plates (for transactivation studies) or at $3 \times 10^6$ cells/150 mm dish (for binding studies) in Dulbecco's modified Eagle medium (high glucose) containing 10% charcoal stripped fetal calf serum, nonessential amino acids, 100 units/ml Penicillin G and 100 mg/ml Streptomycin sulfate (GIBCO BRL) at 37° C. in a humidified atmosphere of 10% $CO_2$. After 24 h, transfections were performed with Lipofectamine (GIBCO BRL) according to the instructions of the manufacturer.

Binding Assays.

Following transfection, cells were grown for 48 h. Receptor preparation and binding methods were based on earlier reports. Cell lysates containing receptor were prepared in TEGM (10 mM Tris, pH 7.2, 1 mM EDTA, 10% glycerol, 7 µl/100 ml β-mercaptoethanol, 10 mM Na molybdate, 1 mM dithiothreotol, 5 µg/ml aprotinin, 2 µg/ml leupeptin, 2 µg/ml benzamide and 0.5 mM PMSF). Plates were placed on ice, rinsed with 10 mM Tris pH 7.2, 50 mM EDTA, 10% glycerol, and scraped into 0.5 ml TEGM. The material was pooled, frozen in liquid nitrogen to lyse the cells, and thawed on ice. The lysate was centrifuged at 228,000× g for 20 min at 4° C. to remove debris and stored frozen (−80° C.) until use. For each assay, an aliquot of receptor containing lysate (0.1–0.25 mg protein) was incubated with 10 nM of labeled thiazolidinedione ([$^3H_2$]AD-5075, 21 Ci/mmole), ±test compound, for ~16 h at 4° C. in a final volume of 300 µl. Unbound ligand was removed by incubation on ice for ~10 min following addition of 200 µl dextran/gelatin-coated charcoal. After centrifugation at 3000 rpm for 10 min at 4° C., 200 µl of the supernatant fraction were counted in a liquid scintillation counter. Nonspecific binding was defined with 10 µM unlabelled AD-5075.

EXAMPLE 4

A patient having a condition characterized by a proliferative, neoplastic disorder is selected for therapy. The patient is treated with a compound identified by the method of Example 1. The treatment is continued until a suitable response is experienced.

What is claimed:

1. A method of treating cancer comprising administering to the patient, in need thereof a pharmaceutical composition comprising a thiazolidinedione in an amount sufficient to modulate PPARγ1 or PPARγ2 activity.

2. The method of claim 1 where the thiazolidinedione is AD-5075, BRL 49653, or CS-045 and the amount of thiazolidinedione administered is about 1 μg to about 100 mg.

3. The method of claim 2 where the pharmaceutical composition is administered subcutaneously, topically, orally, mucosally, intravenously, or intramuscularly.

* * * * *